United States Patent [19]

van Andel

[11] Patent Number: Plant 6,034

[45] Date of Patent: Oct. 6, 1987

[54] ALSTROEMERIA NAMED STALMON

[75] Inventor: Jacob van Andel, Aalsmeer, Netherlands

[73] Assignee: Van Staaveren B.V., Aalsmeer, Netherlands

[21] Appl. No.: 805,210

[22] Filed: Dec. 5, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler; John B. Lungmus

[57] ABSTRACT

A new and distinct variety of Alstroemeria distinguished by having a profuse production of relatively small flowers each having a pink, purple and white coloration and particularly distinguished by having its upper petals of a mainly white color and purple base overcast by short, longitudinally extending pencil stripes of a deep purple color extending from the throat, and the lower petals being of a generally purple color with a pink marginal portion at their outer ends, the blooms being produced the year around and the plant itself having a strong, upright growth habit with a medium production of foliage.

1 Drawing Figure

BACKGROUND OF THE NEW PLANT

This new variety of Alstroemeria originated as a seedling produced by my crossing of my breeding stock variety No. 2771-1 with my stock variety No. 7117-2 in greenhouse at Aalsmeer, The Netherlands, in the course of breeding efforts carried on since 1980 with the object of producing plants having new color and overall flower pattern. This seedling was selected by me for propagation because of the very unusual color pattern of its blossoms and its profuse production of relatively small flowers. Asexual propagation of this new plant was carried on under my direction by root division at Aalsmeer and successive generations of this plant have demonstrated that the distinctive characteristics of the parent hybrid hold true from generation to generation and appear to be firmly fixed. Propagation of this new variety is now being carried on at Aalsmeer by root stock division.

DESCRIPTION OF THE DRAWING

My new Alstroemeria plant is illustrated by the accompanying photographic drawing which shows the distinguishing color characteristics and flower form of the blossoms of this plant, the color rendition being as nearly true as it is reasonably possible to obtain by conventional professional procedures.

DESCRIPTION OF THE NEW PLANT

The following is a detailed description of my new Alstroemeria plant with color designations according to The R.H.S. Colour Chart of The Royal Horticultural Society of London, England.

THE PLANT

Origin: Seedling.

Parentage:

*Seed parent.*—Breeding Stock Variety 2771-1 (unpatented).

*Pollen parent.*—Breeding Stock Variety 7117-2 (unpatented).

Classification:

*Botanic.*—Alstroemeria Hybrid.

*Commercial.*—Alstroemeria.

Form: Bush having tall, slender flowering stalks with flower bearing branches of simple umbel form at its top.

Height: About 120 cm.

Cane length: About 120 cm.

Growth: Strong and upright.

Foliage:

*Quantity.*—Medium.

*Number of leaves.*—Various, depending upon the season.

*Size of leaf.*—Various, depending on season.

*Leaf shape.*—Elliptic.

*Texture.*—Leathery.

*Color.*—Dark green on both upper and under sides.

Rhizomes:

*Color.*—White.

*Size.*—Depends on season.

THE BUD

Form: Pear shaped.

Size:

*Diameter.*—About 20 mm.

*Length.*—About 40 mm.

Opening rate: Normal.

Calyx: This bud has no calyx and the six petals of the flower are a perianth.

Peduncle:

*Length.*—About 50 mm.

*Color.*—Light green.

THE FLOWER

Blooming habit: Continuous and year around.

Flower size: Small.

*Diameter.*—About 45 mm.

*Depth.*—About 50 mm.

Borne: Singly.

Shape: When bloom first opens, cup-shaped. When bloom matures, funnel-like with petal tips curling outward.

Petalage:

*Number of petals.*—Six, arranged in two concentric circles of three each.

*Form.*—Broad oval with obcordate apex.

*Texture.*—Leathery.
*Appearance.*—Shiny.
*Color of Petals.*—72D with 72C in the central area. Reverse side — 71C/D. Upper petals — 65B/C+72C at throat. Reverse side — 72D.

Peduncle:
*Length.*—About 50 mm.
*Color.*—Light green.

Persistence: The petals hang on and dry.

Lasting quality:
*On plant.*—About 15 days.
*As a cut flower.*—About 10 days.

REPRODUCTIVE ORGANS

Stamens:
*Number.*—Six, there being one opposite each petal.

Anthers:
*Color.*—Olive green.

Filaments:
*Color.*—Light purple.

Pistils:

*Number.*—One.
*Color.*—Purple/Pink.

Stigma:
*Color.*—Purple/Pink.

FRUIT

Fertility: The fruit is fertile.
Shape: Capsular.
Color at maturity: Light brown.

This hybrid Alstroemeria is particularly characterized by its relatively small flowers of an unusual pink, purple and white coloration and the overal marking of the upper petals with short, purple, pencil stripes, the flowers being favorable for use as a table decoration.

I claim:

1. A new and distinct Alstroemeria variety, substantially as herein shown and described, particularly characterized by its abundant production of small flowers having a distinctive pink, purple and white coloration.

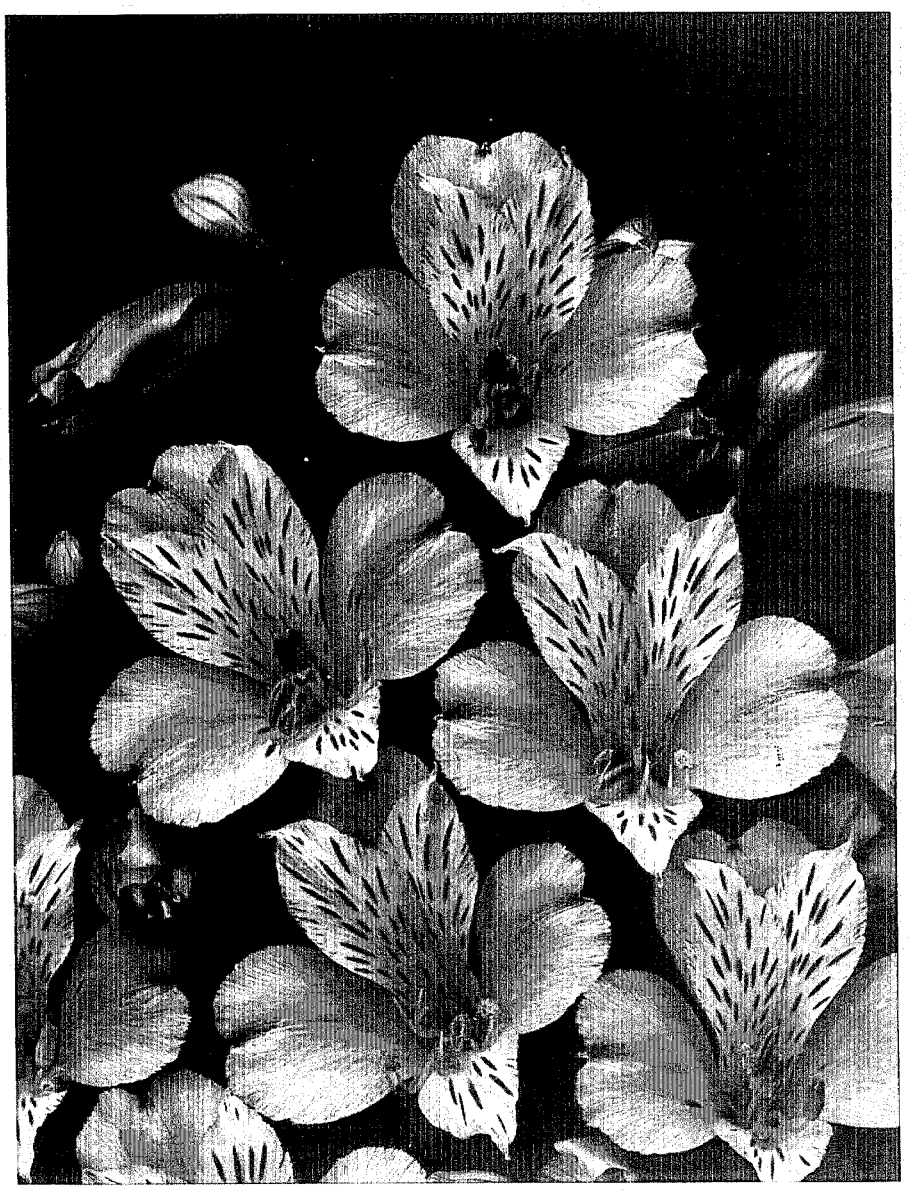

* * * * *